US008027847B1

(12) United States Patent  (10) Patent No.: US 8,027,847 B1
Francis et al.  (45) Date of Patent: Sep. 27, 2011

(54) SYSTEM AND METHOD OF REFILLING A PRESCRIPTION

(75) Inventors: John Brian Francis, Alpharetta, GA (US); John C. Goodwin, III, Suwanee, GA (US)

(73) Assignee: NCR Corporation, Duluth, GA (US)

( * ) Notice: Subject to any disclaimer, the term of this patent is extended or adjusted under 35 U.S.C. 154(b) by 3470 days.

(21) Appl. No.: 10/190,666

(22) Filed: Jul. 9, 2002

(51) Int. Cl.
 *G06Q 10/00* (2006.01)
 *G06Q 50/00* (2006.01)
(52) U.S. Cl. ..................................... 705/2; 705/3; 705/4
(58) Field of Classification Search .................... 705/2–4
 See application file for complete search history.

(56) References Cited

U.S. PATENT DOCUMENTS

| 6,766,218 B2 * | 7/2004 | Rosenblum .................. 700/235 |
| 2002/0032582 A1 * | 3/2002 | Feeney et al. ..................... 705/2 |

* cited by examiner

*Primary Examiner* — Gerald J. O'Connor
*Assistant Examiner* — Linh Michelle Le
(74) *Attorney, Agent, or Firm* — Paul Martin

(57) ABSTRACT

A system and method of refilling a prescription which uses a pharmacy kiosk. One embodiment of the system includes a touch screen located at a pharmacy, an input device in the touch screen or card reader for recording identification information from a customer, a barcode reader located at the pharmacy for reading a barcode containing prescription information from a previous transaction, a card reader or cash acceptor or check reader located at the pharmacy for receiving payment from the customer, and a computer located at the pharmacy for displaying a prompt to enter the identification information and scan the barcode using the touch screen, for recording the prescription information using the barcode reader, for determining corresponding price information for a refill of the prescription, and for processing payment for the refill from the customer.

13 Claims, 3 Drawing Sheets

SYSTEM AND METHOD OF REFILLING A PRESCRIPTION

CROSS-REFERENCE TO RELATED APPLICATIONS

The present invention is related to the following commonly assigned co-pending U.S. applications filed therewith:

Application Ser. No. 10/191,125, entitled "SYSTEM AND METHOD OF COMPLETING A PHARMACY TRANSACTION", having as inventor, John Goodwin;

Application Ser. No. 10/191,234, entitled "SYSTEM AND METHOD OF REFILLING A PRESCRIPTION", having as inventor, John Goodwin;

Application Ser. No. 10/191,236, entitled "SYSTEM AND METHOD OF DETERMINING INTERACTIONS BETWEEN MEDICINES", having as inventor, John Goodwin.

BACKGROUND OF THE INVENTION

The present invention relates to self-service kiosks and more specifically to a system and method of refilling a prescription.

Self-service terminals include kiosks. Kiosks provide a publicly accessible computing platform for displaying World Wide Web (web) pages and other web-delivered content from web sites. Kiosks may be located within a retailer's transaction establishment or elsewhere, such as in shopping malls. Kiosks may be easily networked to web sites using the TCP/IP protocol. Web pages from web sites may be displayed using known and available web software, such as Microsoft® Internet Explorer software.

Major retailers who have pharmacies seek an effective way to complete pharmacy transactions. Pharmacy customers must pay for prescription medicines at store checkout lanes. For customers who only seek to obtain prescription medicine or other pharmacy items, waiting in line at checkout lanes adds extra time to their visits in the store.

Therefore, it would be desirable to provide a system and method of refilling a prescription which allows the pharmacy customer to pay for prescription medicines using a pharmacy kiosk.

SUMMARY OF THE INVENTION

In accordance with the teachings of the present invention, a system and method of refilling a prescription is provided.

One embodiment of the system includes a touch screen located at a pharmacy, an input device in the touch screen or card reader for recording identification information from a customer, a barcode reader located at the pharmacy for reading a barcode containing prescription information from a previous transaction, a card reader or cash acceptor or check reader located at the pharmacy for receiving payment from the customer, and a computer located at the pharmacy for displaying a prompt to enter the identification information and scan the barcode using the touch screen, for recording the prescription information using the barcode reader, for determining corresponding price information for a refill of the prescription, and for processing payment for the refill from the customer.

A method of refilling a prescription includes the steps of displaying a prompt to enter customer identification information by a pharmacy kiosk, recording the customer identification information by the pharmacy kiosk, displaying a prompt to scan a barcode containing prescription information from a previous transaction by the pharmacy kiosk, recording the prescription information by the pharmacy kiosk using the barcode reader, determining corresponding price information for a refill of the prescription by the pharmacy kiosk, and processing payment for the refill by the pharmacy kiosk.

It is accordingly an object of the present invention to provide a system and method of refilling a prescription.

It is another object of the present invention to enable payment for prescription medicines at a pharmacy kiosk.

It is another object of the present invention to use existing self-checkout software to complete payment.

BRIEF DESCRIPTION OF THE DRAWINGS

Additional benefits and advantages of the present invention will become apparent to those skilled in the art to which this invention relates from the subsequent description of the preferred embodiments and the appended claims, taken in conjunction with the accompanying drawings, in which:

DETAILED DESCRIPTION OF THE PREFERRED EMBODIMENT

Figure 1:
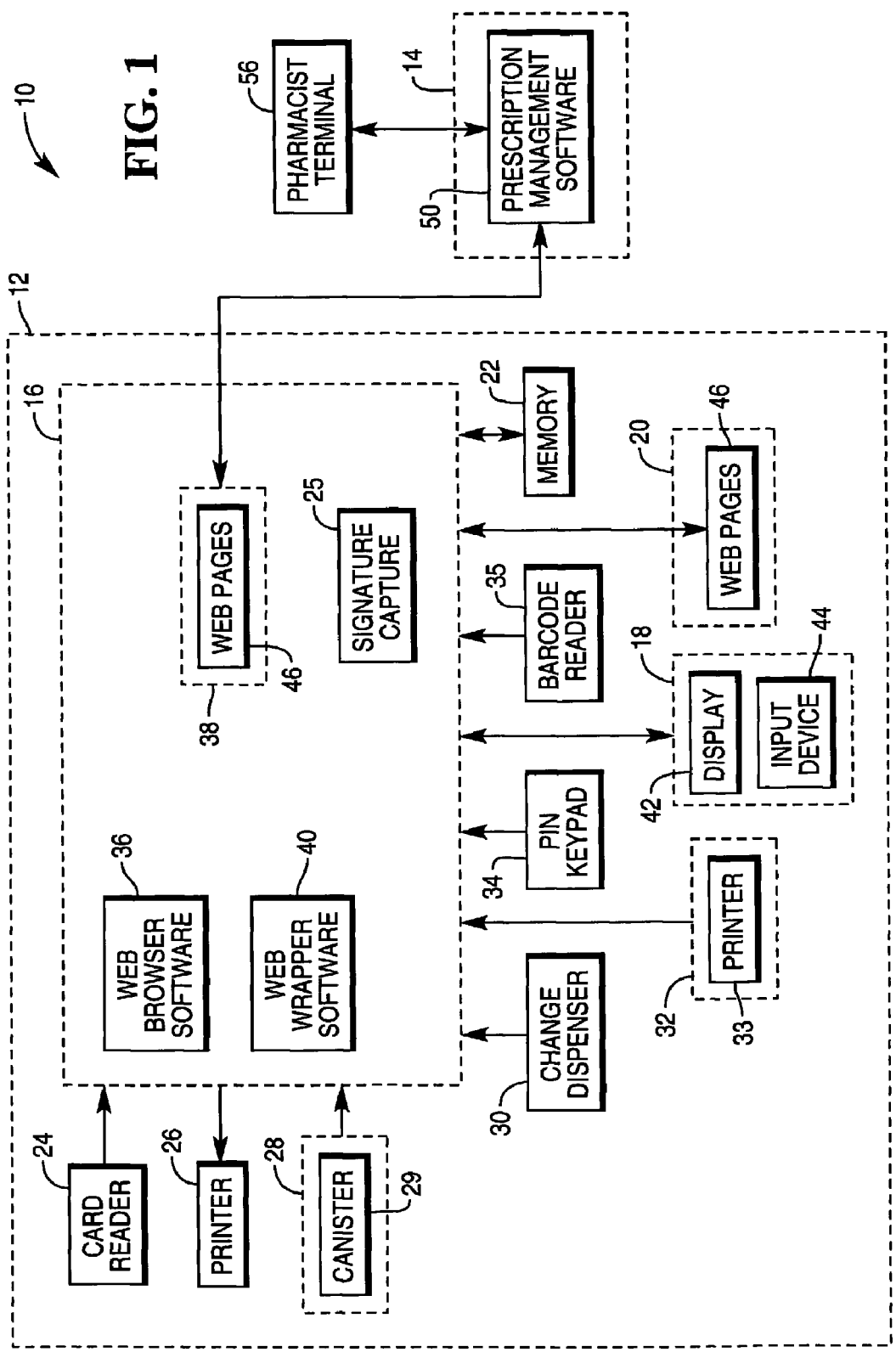
FIG. 1 is a block diagram of a first embodiment of a pharmacy system.
Figure 2:
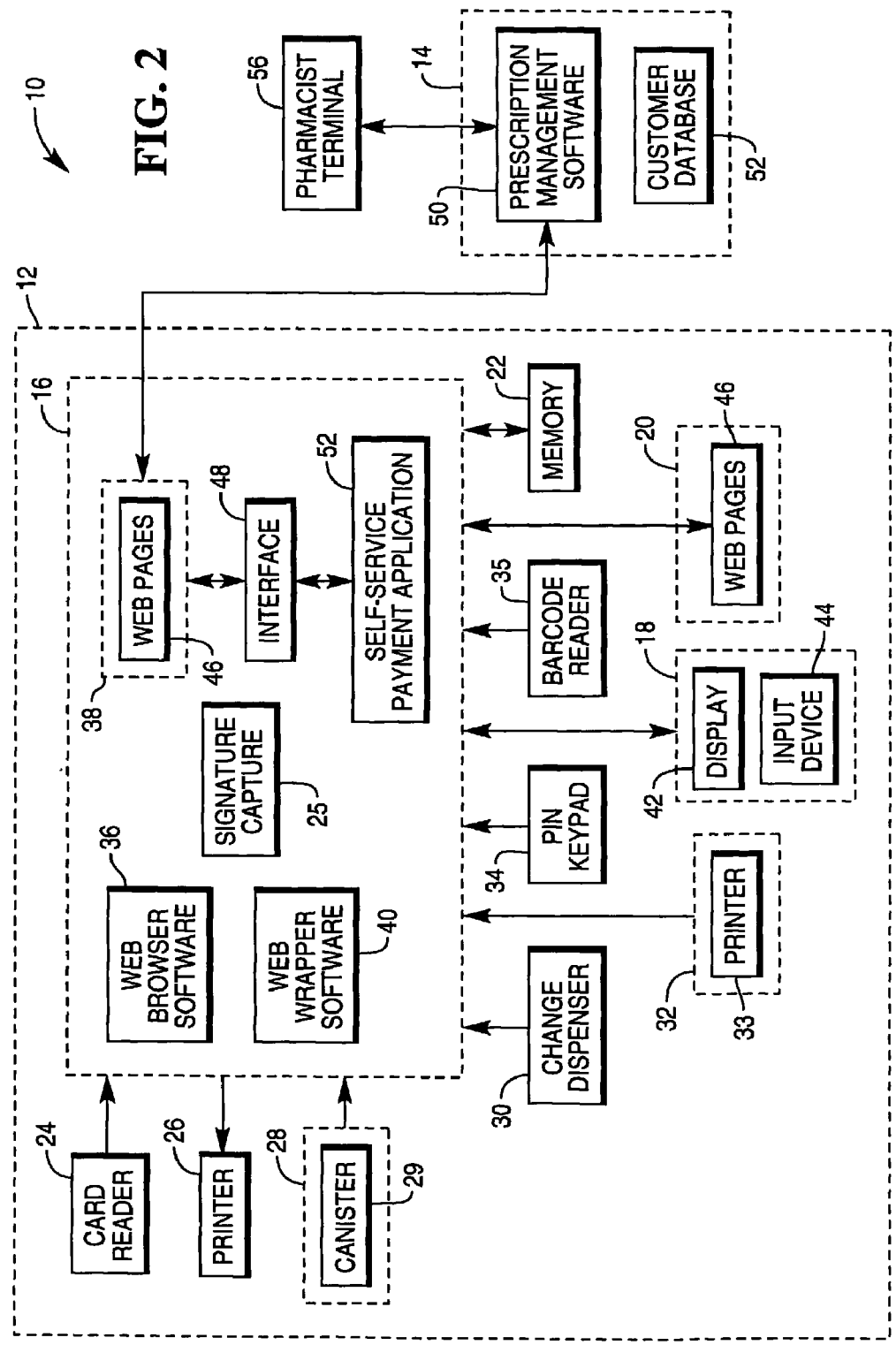
FIG. 2 is a block diagram of a second embodiment of the pharmacy system.
Figure 3:
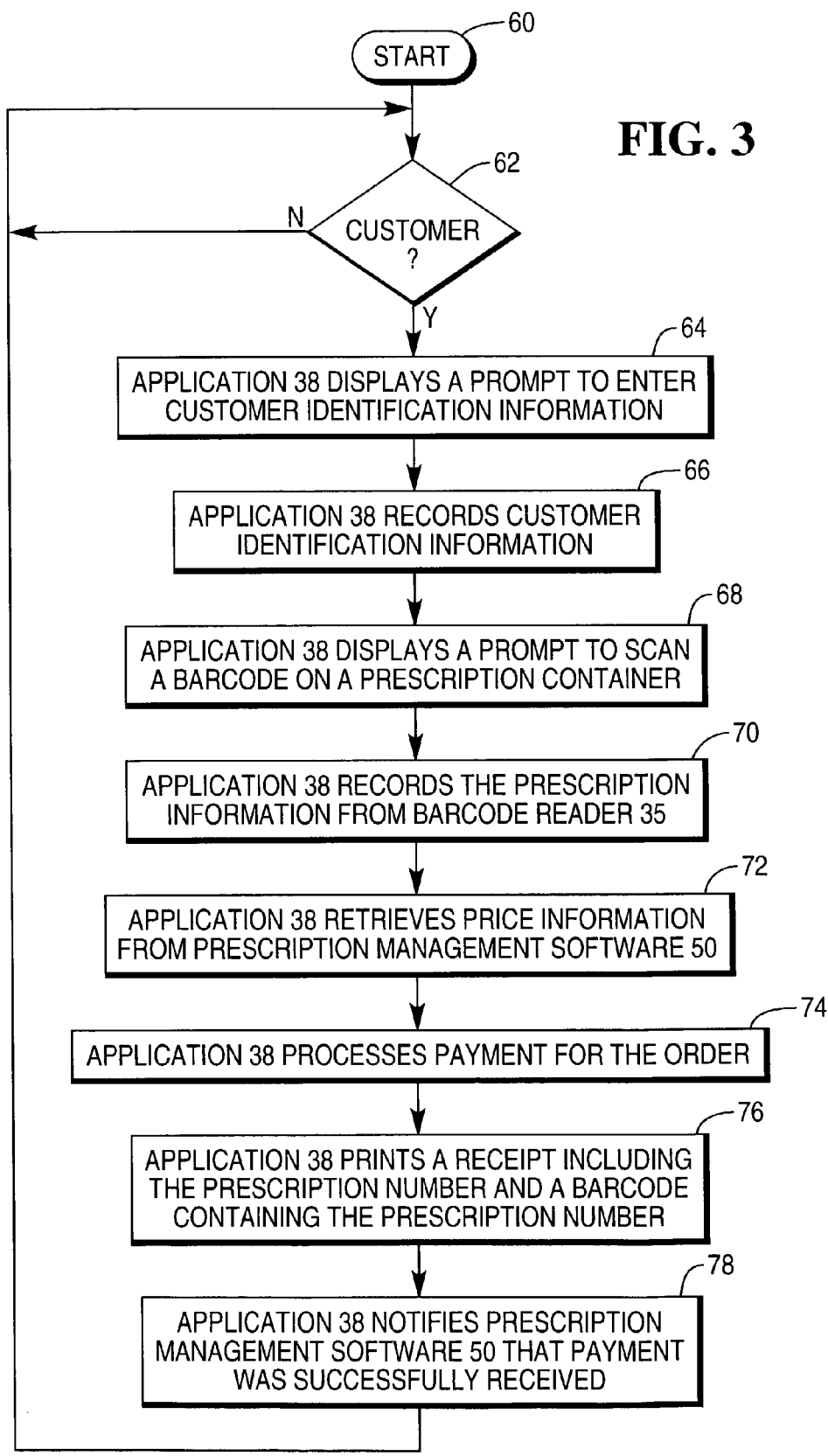
FIG. 3 is a flow diagram illustrating the method of the present invention.

Turning now to FIGS. 1 and 2, system 10 includes kiosk 12 and pharmacy management system 14. Kiosk 12 is preferably located in a retail establishment. Kiosk 12 may include an NCR 7401 computer.

Kiosk 12 is a self-service terminal which primarily includes processor 16, touch screen 18, memory 22, and disk storage 20. Kiosk 12 may optionally include a number of peripherals to enhance operation for ordering and paying for prescription medicine and other pharmacy products. The peripherals may include cash acceptor 28, cash dispenser 30, check reader 32, and personal identification number (PIN) keypad 34.

Under the present invention, kiosk 12 additionally includes barcode reader 35 for scanning barcode labels on medicine containers and receipts from previous transactions. The barcode labels contain prescription identification information.

Processor 16 executes application 38, which guides a customer through a pharmacy transaction. Application 38 records pharmacy customer identification information, retrieves prescription information and cost from pharmacy management system 14, and displays instructions for completing ordering of medications.

In a first embodiment (FIG. 1), application 38 records payment via card reader 24, cash acceptor 28, or check reader 32, and dispenses change through cash dispenser 30. Following receipt of payment, application 38 sends a message to pharmacy management system 14 indicating that the transaction was successful.

In a second embodiment (FIG. 2), application 38 offloads payment processing to self-service payment application 52. Application 38 passes cost details to self-service payment application 52 via interface 48. Following receipt of payment, self-service payment application 52 notifies application 38, which in turn notifies pharmacy management system 14. This embodiment saves development costs for stores by allowing them to use the same application for self-service kiosks and self-service checkout lanes.

In either embodiment, application 38 may record customer signatures and store them electronically for later analysis.

Application 38 may include OPOS (Object Linking and Embedding for Point of Sale) software. OPOS is a technology that enables hardware independence for POS solution providers on Win32 platforms. The industry standard defines a method of interfacing to POS peripherals.

Application 38 communicates with pharmacy management system 14 over a network connection, such as one which uses the TCP/IP protocol. Kiosk 12 may be connected to the World Wide Web (web) and may obtain web content from web servers. Pharmacy management system 14 may be an external web server.

Processor 16 may also execute web browser software 36 and web wrapper software 40.

Web browser software 36 allows an operator to display information in a format established by the World Wide Web (WWW or "web"). Application 38 may be written as a web application which displays pharmacy transaction information in the form of web pages 46, although application 38 may also be a non-web application and operate without web browser software 36 and web wrapper software 40. Web pages 46 may be written using hypertext markup language (HTML) or other suitable web page language.

Web browser software 36 may include commercially available web browser software, such as Microsoft® Internet Explorer web browser software. Microsoft® Internet Explorer web browser software is configured into a kiosk operation using a "-k" command line option. This option hides toolbars and menu bars to prevent operator access to those functions.

Web browser software 36 may also display a start or "home" page within web pages 46 which operates as a default page from which kiosk operation begins and to which operation returns when an operator is finished using kiosk 12. Web browser software 36 may also facilitate purchase of goods from retailers and may also serve to display advertisement when not in use.

Web wrapper software 40 provides security functions. During operation, web wrapper software 40 prevents an operator from accessing kiosk files, or other applications, or the operating system software, or basic input-output system (BIOS) firmware, and prevents the operator from causing kiosk 12 to reboot.

Touch screen 18 includes display 42 and input device 44. Display 42 and input device 44 may also be separate units. Input device 44 may record order selection information from a pharmacy customer.

Disk storage 20 is a first storage medium used by processor 16 which stores web pages 46 for use by application 38 and other applications. Some of web pages 46 may be obtained from web servers.

Memory 22 is a second storage medium used by processor 16 to store executed program information.

Card reader 24 reads loyalty, credit, debit, SMART, and/or other types of cards carried by a pharmacy customer. Card reader 24 may record payment information from a pharmacy customer.

Signature capture unit 25 captures customer signatures.

Printer 26 prints receipt information.

Cash acceptor 28 includes currency storage canister 29. Cash acceptor 28 takes in currency, validates the currency, sends tendered amount information to application 38, and sends currency count information to application 38. Cash acceptor 28 may include a cash acceptor manufactured by CashCode or Mars.

Cash dispenser 30 dispenses change.

Check reader 32 reads checks and includes a magnetic ink character (MICR) reader. Check reader 32 also includes printer 33 for printing information on checks.

PIN keypad 34 records PIN numbers for debit card transactions.

Pharmacy management system 14 executes pharmacy management software 50, which sends price information to kiosk 12 and updates customer accounts following successful payment. Pharmacy management software 50 stores customer identification and order information in customer database 52.

Pharmacist terminal 56 allows a pharmacist to access customer database 52 to determine orders that need filling and whether payment has been made before filling an order. If payment has not been made, then the pharmacist will know to attach a bill or provide other indication that payment must be made before the customer leaves the store.

Turning now to FIG. 2, operation of application 38 is illustrated in detail beginning with START 60.

In step 62, application 38 waits for a pharmacy customer. During this time, kiosk 12 may display advertisements.

In step 64, application 38 displays a prompt to enter customer identification information.

In step 66, application 38 records the customer identification information. Application 38 may record customer information from touch screen 18 or card reader 24.

In step 68, application 38 displays a prompt to scan a barcode on a prescription container or on a receipt from a previous transaction.

In step 70, application 38 records the prescription information from barcode reader 35. Application 38 may use OPOS software to decode and then parse then decoded information from the OPOS software.

In step 72, application 38 retrieves price information from prescription management software 50.

In step 74, application 38 processes payment for the order. In a first embodiment, application 38 processes payment directly. In a second embodiment, application 38 passes order details to self-service payment application 52 via interface 48. Application 38 receives notification of successful payment from self-service payment application 52. In either embodiment, application 38 may record customer signatures and store them electronically for later analysis.

In step 76, application 38 prints a receipt including the prescription number and a barcode label containing the prescription number.

In step 78, application 38 notifies prescription management software 50 that payment was successfully received. Prescription management software 50 updates the customer's account in customer database 52. A pharmacist may access customer database 52 through pharmacist terminal 56 to verify that payment has been received before filling the order. Operation returns to step 62 to wait for the next customer.

Although the present invention has been described with particular reference to certain preferred embodiments thereof, variations and modifications of the present invention can be effected within the spirit and scope of the following claims.

We claim:

1. A method of refilling a prescription comprising the steps of:
   (a) displaying a prompt to enter customer identification information by a pharmacy kiosk;
   (b) recording the customer identification information by the pharmacy kiosk;

(c) displaying a prompt to a user to scan a barcode containing prescription information on a container from a previous refill transaction by the pharmacy kiosk;
(d) recording the prescription information by the pharmacy kiosk using the barcode reader;
(e) determining corresponding price information for a refill of the prescription by the pharmacy kiosk; and
(f) processing payment for the refill by the pharmacy kiosk.

2. The method as recited in claim 1, wherein step b) comprises the step of:
(b-1) recording the customer identification information by a card reader of the pharmacy kiosk.

3. The method as recited in claim 1, wherein step (b) comprises the step of:
(b-1) recording the customer identification information by a touch screen of the pharmacy kiosk.

4. The method as recited in claim 1, wherein step (e) comprises the step of:
(e-1) determining corresponding price information from a prescription management server.

5. The method as recited in claim 1, wherein step (f) comprises the step of:
(f-1) processing payment by pharmacy transaction software executed by the pharmacy kiosk.

6. The method as recited in claim 1, wherein step (f) comprises the step of:
(f-1) processing payment by self-service transaction software through an interface to pharmacy transaction software executed by the pharmacy kiosk.

7. The method as recited in claim 1, wherein step (f) comprises the step of:
(f-1) capturing a customer signature by a signature capture unit of the pharmacy kiosk.

8. The method as recited in claim 1, further comprising the step of:
(g) notifying a prescription management server that payment was successfully made by the pharmacy kiosk.

9. The method as recited in claim 8, further comprising the step of:
(h) updating a customer account in a database by a pharmacy management server.

10. The method as recited in claim 9, further comprising the step of:
(i) displaying payment information in the customer account by a pharmacist terminal to verify that the payment was made.

11. A method of refilling a prescription comprising the steps of:
(a) displaying a prompt to enter customer identification information by a pharmacy kiosk;
(b) recording the customer identification information by the pharmacy kiosk;
(c) displaying a prompt to scan a barcode containing prescription information from a previous transaction by the pharmacy kiosk;
(d) recording the prescription information by the pharmacy kiosk using the barcode reader;
(e) determining corresponding price information for a refill of the prescription by the pharmacy kiosk;
(f) processing payment by pharmacy transaction software executed by the pharmacy kiosk;
(g) notifying a prescription management server that payment was successfully made by the pharmacy kiosk;
(h) displaying the payment status to a pharmacist; and
(i) dispensing the prescription refill after the payment status has been viewed.

12. A method of refilling a prescription comprising the steps of:
(a) displaying a prompt to enter customer identification information by a pharmacy kiosk;
(b) recording the customer identification information by the pharmacy kiosk;
(c) displaying a prompt to a user to scan a barcode containing prescription information from a previous transaction by the pharmacy kiosk;
(d) recording the prescription information by the pharmacy kiosk using the barcode reader;
(e) determining corresponding price information for a refill of the prescription by the pharmacy kiosk;
(f) processing payment for the refill by the pharmacy kiosk;
(g) notifying a prescription management server that the payment was successfully made by the pharmacy kiosk;
(h) updating a customer account in a database by the pharmacy management server; and
(i) displaying payment information in the customer account by a pharmacist terminal to verify that the payment was made.

13. A method of refilling a prescription comprising the steps of:
(a) displaying a prompt to enter customer identification information by a pharmacy kiosk;
(b) recording the customer identification information by the pharmacy kiosk;
(c) displaying a prompt to a user to scan a barcode containing prescription information on a receipt from a previous refill transaction by the pharmacy kiosk;
(d) recording the prescription information by the pharmacy kiosk using the barcode reader;
(e) determining corresponding price information for a refill of the prescription by the pharmacy kiosk; and
(f) processing payment for the refill by the pharmacy kiosk.

* * * * *